(12) United States Patent
Cloidt et al.

(10) Patent No.: US 8,425,626 B2
(45) Date of Patent: Apr. 23, 2013

(54) METHOD FOR PROCESSING MOLASSES

(75) Inventors: Roland Cloidt, Radeberg (DE); Hanno Lehmann, Sundern (DE)

(73) Assignee: Molkerei Alois Muller GmbH & Co. KG, Aretsried (DE)

( * ) Notice: Subject to any disclaimer, the term of this patent is extended or adjusted under 35 U.S.C. 154(b) by 873 days.

(21) Appl. No.: 12/572,898

(22) Filed: Oct. 2, 2009

(65) Prior Publication Data
US 2011/0081695 A1 Apr. 7, 2011

(51) Int. Cl.
*B01D 9/00* (2006.01)
(52) U.S. Cl.
USPC ............... 23/297; 23/295 R; 23/299
(58) Field of Classification Search ............ 23/295 R, 23/297, 299
See application file for complete search history.

(56) References Cited

U.S. PATENT DOCUMENTS
2,584,158 A 2/1952 Pratt et al.

FOREIGN PATENT DOCUMENTS
GB 1 575 089 A 9/1980

OTHER PUBLICATIONS

Caric Marijana: "Concentrated and dried dairy products, Lactose" Concentrated and Dried Dairy Products, VCH Publishers, New York, NY, US, 1991, Seiten 227-234, XP002410105.

*Primary Examiner* — Edward Johnson
(74) *Attorney, Agent, or Firm* — Schwabe, Williamson & Wyatt, P.C.

(57) ABSTRACT

A method of processing residual molasses from a procedure for the production of lactose from whey permeate. From this molasses, a mineral diminished component is extracted, concentrated, crystallized and therefrom a crystallized phase is separated.

29 Claims, 2 Drawing Sheets

METHOD FOR PROCESSING MOLASSES

BACKGROUND OF THE INVENTION

The invention concerns a method for processing molasses, which is left as a residual liquid after a treatment of whey. In the said treatment, the whey is separated by membrane filtration into a protein-enriched retentate and a lactose intensified permeate. This permeate is evaporated and crystallized, allowing lactose to be recovered by a mechanical separator, whereby molasses constitutes an unwanted runoff.

SUMMARY OF THE INVENTION

This present invention has the purpose of creating a method for the processing this molasses, wherein the molasses can be advantageously converted into valuable substances.

This purpose can be achieved, in accordance with the invention, by a method including the following steps:
the recovery of a component of diminished mineral content by separation of same from the molasses;
the concentration of the diminished mineral component by dewatering and crystallizating the concentrated components;
the separation of a precipitated crystalline substance from a liquid phase subjected to crystallization;
a washing of the so separated crystalline substance with an appropriate washing fluid.

As an example, molasses from the above procedure possesses a dry weight content within a range of 18 to 35%. A diminished mineral content of the molasses, which is due to the removal of a component high in minerals, provides an advantageous property for a crystallization procedure which follows:

Electrodialysis or chromatography serve well for the removal of minerals on a commercial scale. Mineral containing components found in molasses are thus removed to the extent of a maximum of 50 to 80%, or in general industrial practice, to about 60 to 65%. Advantageously, to take full advantage of a removal operation, the molasses should be adjusted, for example, to a dry weight basis of 10%. The molasses under treatment can be subjected to the addition of waste steam, which is generated in a yet to be described step of the process. By this addition of steam, the water balance of the entire process is brought into equilibrium and no additional fresh water need be added.

For example, the demineralized component, isolated from the electrolysis/chromatography step, shows a dry weight reading of approximately 20%. Glucose and lactic acid in the dry material analyze at 2 to 5% and the dry material ash content runs about 8 to 9%.

The dry matter content of the demineralized component can be increased to 60 to 70% by evaporation.

Crystallization of the component in this manner is advantageously carried out in a crystallizing tank, wherein a normal charge may take some 25 to 35 hours.

The thereby formed crystalline suspension can be treated either in accordance with EP 1878340, "A Process for the Preparation of Whey Permeate Powder" or alternately, the treatment may follow the course of the following procedure:

The suspension, including the finely divided crystalline phase, is directed to repetitive process steps, these being advantageously a series of 2-stage or 4-stage decanter and wash units. In such a stepped procedure, all interfering contaminants are removed. The thus removed contaminants still bear glucose and lactic acid, which substances do not react well in a drying operation. These contaminants consist of only 1% or advantageously as low as 0.2%. However, the stated low percentage allows these materials to under go a drying operation, from which the end product is lactose powder.

Especially advantageously, three byproducts can be reprocessed into ethanol, these being first, the liquid phase which is separated from the said crystal suspension; second, the component carrying glucose and lactic acid; and third, the component containing removed mineral.

BRIEF DESCRIPTION OF THE DRAWINGS

The invented procedure is described and explained in the following with the aid of attached drawings. There is shown in.

DETAILED DESCRIPTION OF THE EMBODIMENTS OF THE INVENTION

Figure 1:
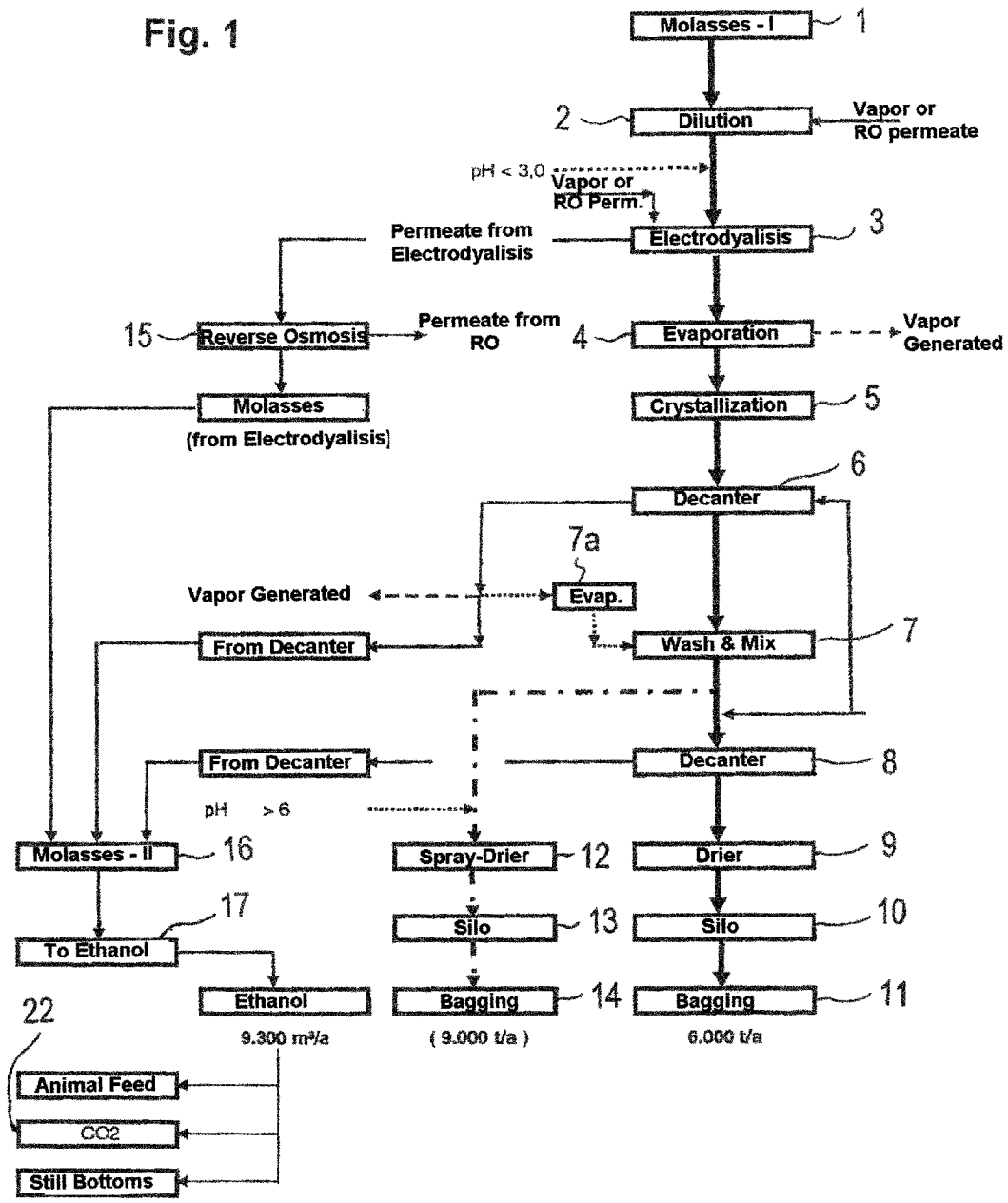
FIG. 1 a flow sheet of the invented process in its entirety.

In the flow sheet of FIG. 1, Step 1 symbolizes the input feed of molasses at the start of the invented process. This molasses originates at the conclusion of a procedure for the production of lactose. In that lactose production process, a protein-enriched, retentate is removed. Lactose is yielded from the resulting lactose rich permeate by evaporation to a crystallization point thereof. In Step 2, the molasses from Step 1, which has a dry weight of some 25%, is adjusted downward to a standard dry weight level of 10% or less by permeate/water dilution. The diluting means may be further defined as waste steam influx and/or permeate from reverse osmosis, both of which occur in subsequently described steps of the process.

Molasses, standardized as stated above, is brought to a pH value between 2 and 6 by the addition of an appropriate substance, for example, hydrochloric acid. In Step 3, preferably at pH 2, electrodialysis removes approximately 60 to 65% of the mineral content, which is a preponderant amount of inorganic substances. Recommendation is made, that prior to electrodialysis, the molasses should be subjected to mechanical clarification, preferably in a separator or by microfiltation. Such clarification restrains particulate, which could act negatively on electrodialysis. The now demineralized component which follows electrodialysis will show a dry weight of about 20%. In Step 4, evaporation takes place, bringing the dry material weight up to 65%. At this concentration, the molasses is conducted to a crystallizer in Step 5, wherein crystallization takes place during some 25 to 35 hours.

Steps 6 and 7 represent the multi-operational wash sequence, followed by decantation in step 8. In these successive steps, minerals, proteins, glucose and lactic acid are principally removed. These materials are considered undesirable in an eventual dried product. The remaining outflow from Step 8, now carries about 1%, preferably only 0.5%, of the original objectionable materials, is conducted to a dryer in Step 9. The output of this dryer is lactose powder and is sent to Step 10 for silo storage, from which the powder is conveyed to Step 11 for commercial bagging.

Advantageously, the process is so designed, that, dependent upon the market, permeate powder or a higher grade lactose powder can be produced. To achieve this, mixture coming from wash & mix Step 7 at a pH of 6 or higher, can be entirely, or partially dried in a spray dryer represented by Step 12. The resulting powder, so dried, is then collected in silo 13 to be conveyed for bagging as output in Step 14.

The evaporative steam from the Steps 4 and 7a is recycled back to the dilution Step 2, to the electrodialysis of Step 3 and to the decanter/wash Steps 6, 8. Because of this reflux of steam, generated as the process runs through the described Steps 1 to 8, no fresh water need be added.

The residual component found in electrodialysis Step 3, during recovery of the demineralized material, is concentrated by reverse osmosis in Step 15 and the concentrate therefrom, i.e. the retentate, is sent to a process for conversion to ethanol. To maintain a material balance, the permeate of Step 15 is returned to the dilution Step 2, to the electrodialysis Step 3 and to the decanter operations of Steps 6 and 8.

In a diversion from Step 6, that part of the liquid phase, which is not intended to be forwarded to Step 7, is conducted to the ethanol generating process starting in Steps 16 and 17. This diverted part runs about 70 to 90%, more practically 85% and removes amorphous lactose and galactose from the flow process steps in the section between Steps 1 to 8.

Further, separated-out liquid phase from the decanter of Step 8 is routed to the process for ethanol production. The combination of three streams, as shown on the flow chart in FIG. 1, which comprise products from: first, the electrodialysis Step 3, the decanter Step 6, and the decanter Step 8, is shown in the flow chart of FIG. 1 as a single input material flow to the ethanol process. This is illustrated in FIG. 1 by the Steps 16 and 17.

Figure 2:
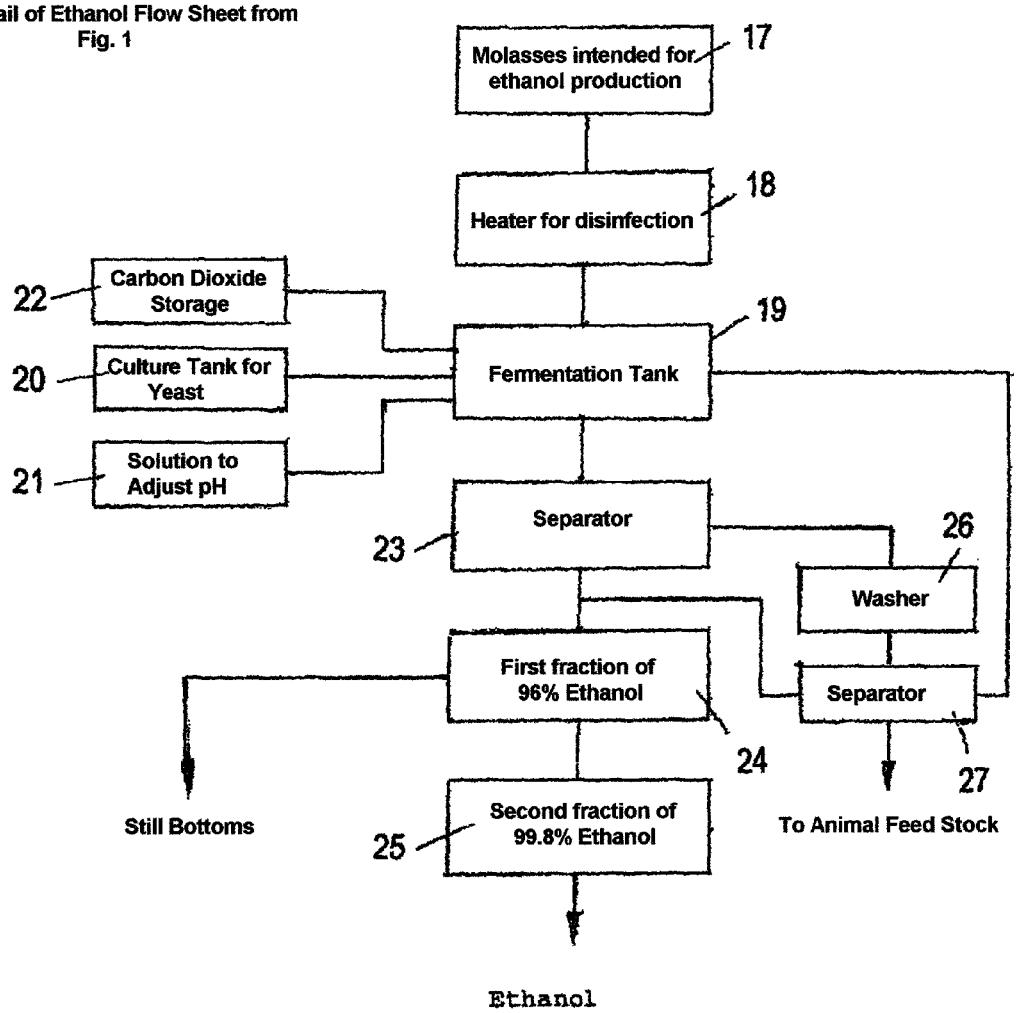
FIG. 2 details of the branch from FIG. 1 showing the production of ethanol.

In accordance with FIG. 2, a detail of the function in and following Step 17 is diagrammed and explained. Step 17 represents a tank, wherein the output stream therefrom is directed to a heating element Step 18. In Step 18 input material is heated in an exchanger to a temperature of 85° C. to enhance germ destruction. Following the heating equipment of Step 18, is a fermentation tank 19 to which yeast is added from a culturing tank 20 and fermentation takes place at a temperature of 25 to 35° C. The yeast can advantageously be of the type kluyveromyces. The adjustment of an appropriate pH value, for example, this could be in the range of 4 to 6, is carried out by the addition of a base or acid additive, which can be contained in a storage tank represented by Step 21. The carbon dioxide, which is generated during the fermentation is captured and liquefied in an appropriate container 22.

When fermentation is considered to be complete, the fermented under layer is conducted into a separator 23 and divided into a yeast concentrate and a yeast-free fermentate. The yeast free part is directed to Step 24 wherein a raw alcohol is generated by rectified distillation. This alcohol, which analyzes up to 96% is transferred to a subsequent dehydration stage in Step 25, wherein the alcohol content is raised to at least 99.8%. This final alcohol product meets the requirements of approved commercial ethanol.

The remaining yeast concentrate in the separator 23 is diluted with water and transferred to a second separator 27 for concentration. The clear phase from the said second separator 27 is caused to mix with the fermentate from separator 23 being fed into distillation Step 24, whereby a recovery of residual alcohol is achieved. The yeast concentrate in the separator 27 is returned up to 50% into the fermentation tank 19. The yeast concentrate, which is not recycled is disposed of as an animal feed.

The still-bottom sludge, which remains from the distillation-rectification equipment of Step 24, is removed and can be concentrated for additional use by evaporation to 20 to 30% dry weight content.

In FIG. 1, is shown, for example, the yearly output for a process run on an industrial commercial scale. In accordance therewith, from a yearly input of 29,986 (metric) tons of molasses per year, the following can be obtained: 6,000 tons lactose powder or alternately 9,000 tons permeate powder and 9,300 cubic meters of ethanol.

The invention claimed is:

1. A method for processing molasses, which includes the following steps:
   isolation of a molasses component having mineral content diminished by water removal,
   crystallization of a concentrated component,
   separation of a deposited crystallized phase from a liquid phase, and
   washing the deposited crystallized phase with a washing solution, wherein the residual component remaining after the above said isolation of the diminished mineral content is reprocessed to ethanol.

2. A method for processing of molasses, in accordance with claim 1, which includes the following steps:
   isolation of a molasses component of diminished mineral content by removal of minerals from the molasses,
   concentration of the diminished mineral content by dewatering,
   crystallization of the concentrated component,
   separation from the liquid of crystalline phase deposited from the crystallization operation, and
   washing the separated crystalline phase with a washing solution, wherein a component formed from at least one part of the liquid phase of the crystallization procedure is reprocessed to ethanol.

3. A method for processing molasses, in accordance with claim 1, including the following steps:
   isolation of a molasses component of diminished mineral content by removal of minerals from the molasses,
   concentration of the diminished mineral content by dewatering,
   crystallization of the concentrated component,
   separation of deposited crystalline phase from the liquid phase, and
   washing the separated crystalline phase with a washing solution, wherein by subjecting the washed crystalline phase to a separator, a component of diminished glucose and lactic acid is obtained and following separation, the residual component containing glucose and lactic acid is further processed to ethanol.

4. A method in accordance with claim 1, wherein the separation of minerals from the molasses is carried out by electrodyalisis.

5. A method in accordance with claim 1, wherein the separation of minerals from the molasses is carried out by chromatography.

6. A method in accordance with claim 1, wherein the concentration of the diminished mineral content component is done by evaporation.

7. A method in accordance with claim 1, wherein the crystallization is carried out in a crystallization tank.

8. A method in accordance with claim 1, wherein the separation of the crystalline phase is carried out in a decanter.

9. A method in accordance with claim 1, wherein the mixed liquid from the liquid phase of the crystallization process is removed.

10. A method in accordance with claim 9, wherein the removed liquid phase for is concentrated to produce the mixed liquid.

11. A method in accordance with claim 10, wherein the concentration of the said removed liquid phase is carried out by evaporation.

12. A method in accordance with claim 1, wherein the molasses, which has been fed to the process possesses a dry weight between 18 and 35%.

13. A method in accordance with claim 1, wherein the dry weight value of the molasses which has been fed to the process is adjusted to 10% or less.

14. A method in accordance with claim 12, wherein the adjustment of the dry weight value is effected by the input of at least one evaporation step producing the steam which arises from the process.

15. A method in accordance with claim 1, wherein the concentrated component has a dry weight value between 60 and 70%

16. A method in accordance with claim 1, wherein by means of the separation, between 60 and 65% of the minerals contained in the input molasses is removed.

17. A method in accordance with claim 1, wherein the crystallation requires 25 to 35 hours to take place.

18. A method in accordance with claim 1, wherein to carry out the isolation of the component of diminished mineral content, the pH value is adjusted to less than 6.0.

19. A method in accordance with claim 3, wherein the separation of the component, which is diminished in glucose and lactic acid, is carried out in a decanter.

20. A method in accordance with claim 3, wherein the component, which is diminished in glucose and lactic acid, is dried.

21. A method in accordance with claim 1, wherein the washed crystalline phase is spray dried.

22. A method in accordance with claim 21, wherein the pH value of the washed crystallized phase is adjusted to 6 or higher.

23. A method in accordance with claim 1, wherein the component, which is to be reprocessed to alcohol, after addition of yeast, is fermented, subsequently an alcoholic component therefrom is mechanically separated from the yeast and thereafter, an alcoholic fraction is yielded from the yeast-free alcoholic component by thermal means.

24. A method in accordance with claim 23, wherein the mechanical separation is carried out by a separator.

25. A method in accordance with claim 23, wherein the thermal separation of the alcohol fraction is carried but by distillation.

26. A method in accordance with claim 23, wherein the said thermal means for separation encompasses a rectification.

27. A method in accordance with claim 23, wherein the said yeast contains the species kluyveromyces.

28. A method in accordance with claim 23, wherein a portion of the mechanically separated yeast is returned to the fermentation step.

29. A method in accordance with claim 1, wherein the molasses which has been feed stock to the process is derived from a whey treatment system, wherein the whey is first extracted from protein by a high-order membrane filtration and finally separated from lactose by a crystallization procedure, from which extractions the mother-liquor is designated as the molasses of the described process.

* * * * *